United States Patent [19]
Grollier

[11] Patent Number: 4,857,303
[45] Date of Patent: Aug. 15, 1989

[54] DENTIFRICE GEL
[75] Inventor: Jean F. Grollier, Paris, France
[73] Assignee: L'Oreal, Paris, France
[21] Appl. No.: 95,858
[22] Filed: Sep. 14, 1987
[30] Foreign Application Priority Data
  Sep. 17, 1986 [LU] Luxembourg .................. 86596
[51] Int. Cl.$^4$ .................. A61K 7/16; A61K 7/18; A61K 7/22
[52] U.S. Cl. .................. 424/52; 424/49; 424/54; 424/57
[58] Field of Search .................. 424/49–58
[56] References Cited
U.S. PATENT DOCUMENTS

| | | |
|---|---|---|
| 3,578,719 | 5/1971 | Kalopissis et al. .................. 260/611 |
| 3,678,155 | 7/1972 | Clippingdale et al. .................. 424/52 |
| 3,821,372 | 6/1974 | Vanlergerghe et al. .................. 424/170 |
| 3,957,968 | 5/1976 | Cordon .................. 424/57 |
| 4,024,239 | 5/1977 | Pader .................. 424/57 |
| 4,168,301 | 9/1979 | Pugh et al. .................. 424/49 |
| 4,307,079 | 12/1981 | Zorayan et al. .................. 424/70 |
| 4,710,374 | 12/1987 | Grollier et al. .................. 514/881 |

FOREIGN PATENT DOCUMENTS
2136689 9/1984 United Kingdom .
2140691 12/1984 United Kingdom .
2193501 2/1988 United Kingdom .

Primary Examiner—Shep K. Rose
Attorney, Agent, or Firm—Fleit, Jacobson, Cohn, Price, Holman & Stern

[57] ABSTRACT

Dentifrice composition, characterized in that it takes the form of a creamy gel containing at least one abrasive agent and at least one thickening agent which results from the ionic interaction in aqueous medium between a cationic polymer, consisting of a copolymer of cellulose or cellulose derivative grafted with a water-soluble quaternary ammonium monomer salt, and a carboxylic anionic polymer having an absolute capillary viscosity in dimethylformamide or methanol, at a concentration of 5% and at 30° C., of less than or equal to 0.08 Pa.s, this thickener having an Epprecht-Drage, module 3, viscosity in 1% strength solution in water at 25° C. greater than or equal to 0.45 Pa.s.

12 Claims, No Drawings

DENTIFRICE GEL

The invention relates to a creamy dentifrice gel containing at least one abrasive agent and one thickening agent.

Dentifrices are well known in the state of the art, and they have to combine many qualities from the standpoint of both appearance, such as homogeneity, of rheological properties, of preservation, of foaming power, of their cleaning and polishing properties and of their abrasive nature.

In particular, compositions are sought which are smooth, homogeneous and shiny, and have constant viscosity and a consistency suitable for forming a ribbon which adheres to the toothbrush without, however, spreading excessively, with a high capacity for cleaning and polishing so as to impart a high lustre to the enamel while showing little abrasive action with respect to the dentine.

Various dentifrice compositions are known, such as compositions based on α-alumina trihydrate, containing thickening agents such as, for example, natural or synthetic gums such as xanthan gum and cellulose gums including hydroxymethylcarboxyethylcellulose, hydroxyethylcellulose and more especially sodium carboxymethylcellulose.

Some of these compositions of the prior art are thick pastes, of matt appearance, and in some cases difficult to squeeze from a tube or a pump dispenser. Moreover, they sometimes adhere poorly to the brush and impart roughness to the teeth and the buccale mucosa after brushing.

Others have a matt granular appearance with a non-uniform viscosity, or do not disperse readily in water during rinsing.

Dentifrice compositions are also known which contain an α-alumina trihydrate combined with hydrated silica and which have the texture of a gel that can be readily squeezed from tubes, but these leave a powdery deposit in the mouth which crunches under the teeth.

The Applicant has just discovered that a dentifrice composition containing an abrasive, not possessing the abovementioned disadvantages, could surprisingly be obtained by using in this composition a thickening agent resulting from the ionic interaction in aqueous medium between a quaternary polymer, consisting of a copolymer of cellulose or cellulose derivative grafted with a water-soluble quaternary ammonium monomer salt, and a carboxylic anionic polymer.

The composition according to the invention makes it possible, in particular, to prepare a shiny, homogeneous and smooth dentifrice composition in gel form, possessing a creamy texture and having constant viscosity, and which is easily squeezed from a tube to form a ribbon that adheres well on the brush without spreading excessively.

The dentifrice compositions according to the invention enable good cleaning and good polishing of the teeth to be obtained, leaving them smooth and gleaming. Moreover, their good rheological properties enable them to be made more effective for oral cleaning in the spaces between the teeth.

The subject of the invention is hence a dentifrice composition containing at least one abrasive and, by way of a thickening agent, the product resulting from the ionic interaction in aqueous medium between a copolymer of cellulose or of a cellulose derivative, grafted with a water-soluble quaternary ammonium monomer salt, and a carboxylic anionic polymer.

Another subject of the invention consists of the process for cleaning the teeth employing this composition.

Other subjects of the invention will become clear on reading the description and the examples which follow.

The dentifrice composition according to the invention is essentially characterized in that it takes the form of a creamy gel containing at least one abrasive and at least one thickening agent, which is a product resulting from the ionic interaction in aqueous medium between a copolymer of cellulose or of a cellulose derivative, grafted by means of a free-radical reaction with a water-soluble quaternary ammonium monomer, and a carboxylic anionic polymer possessing an absolute capillary viscosity, when diluted in dimethylformamide or methanol to a concentration of 5% and at a temperature of 30° C., of less than or equal to 0.08 Pa.s.

The thickener preferably has an Epprecht-Drage, module 3, viscosity at 21° C., measured when diluted in water to a concentration of 1%, equal to or greater than 0.450 Pa.s.

The cationic polymer used for preparing the thickener is more especially chosen from the polymers of cellulose derivatives consisting of hydroxyalkylcelluloses, such as hydroxymethylcellulose, hydroxyethylcellulose or hydroxypropylcellulose, grafter by means of a free-radical reaction with a water-soluble quaternary ammonium monomer salt chosen from methacryloylethyltrimethylammonium, methacrylamidopropyltrimethylammonium and dimethyladiallylammonium salts, and more especially the halides such as the chlorides or alternatively methosulphates.

Special preference is given to products consisting of the copolymer of hydroxyethylcellulose grafted by means of a free-radical reaction with diallyldimethylammonium chloride, sold under the name "CELQUAT L 200" or "CELQUAT H 100" by the company NATIONAL STARCH, or alternatively referred to in the CTFA dictionary as "Polyquaternium 4". These polymers, when diluted in water to a concentration of 1% and at a temperature of 30° C., have an absolute capillary viscosity of the order of 0.01 Pa.s for the product marketed under the name "CELQUAT L 200" and 0.02 Pa.s for the product marketed under the name "CELQUAT H 100".

The anionic polymers used according to the invention are carboxylic anionic polymers having a molecular weight of between 500 and 3,000,000 and more especially between 1,000 and 3,000,000. These are preferably film-forming polymers. Special preference is given to anionic polymers chosen from:

(a) homopolymers of methacrylic acid having a molecular weight, determined by light scattering, of more than 20,000;

(b) copolymers of methacrylic acid with one of the following monomers:
   $C_1$–$C_4$ alkyl acrylate or methacrylate;
   an acrylamide derivative such as, more especially, N,N-dimethylacrylamide, diacetoneacrylamide or N-tert-butylacrylamide;
   maleic acid;
   $C_1$–$C_4$ alkyl monomaleate;
   N-vinylpyrrolidone;

(c) copolymers of ethylene and maleic anhydride such as the products sold under the name EMA 31 by the company MONSANTO Cie.

The anionic polymers which are especially preferred for producing the thickening agent used according to the invention are copolymers of methacrylic acid possessing an absolute capillary viscosity, measured in solution in dimethylformamide or methanol at a concentration of 5%, at 30° C., of between 0.003 and 0.080 Pa.s, and more especially the copolymer of methacrylic acid and methyl methacrylate whose absolute capillary viscosity, measured in solution in dimethylformamide at a concentration of 5%, is of the order of 0.015 Pa.s; the copolymers of methacrylic acid and ethyl monomaleate possessing an absolute capillary viscosity, measured in solution in dimethylformamide at a concentration of 5%, of the order of 0.013 Pa.s; the copolymers of methacrylic acid and butyl methacrylate whose absolute capillary viscosity, measured in solution in methanol at a concentration of 5%, is of the order of 0.010 Pa.s; the copolymers of methacrylic acid and maleic acid whose absolute capillary viscosity, measured in solution in dimethylformamide at a concentration of 5%, is of the order of 0.016 Pa.s; the copolymers of methacrylic acid and diacetoneacrylamide whose absolute capillary viscosity, measured in solution in methanol at a concentration of 1%, is of the order of 0.009 Pa.s; and polymethacrylic acid of molecular weight 137,000 whose absolute capillary viscosity, measured in solution in methanol at a concentration of 5%, is of the order of 0.068 Pa.s.

The thickener may be prepared under the following conditions: to the copolymer of cellulose or of a cellulose derivative, grafted by means of a free-radical reaction with a water-soluble quaternary ammonium monomer salt, the quantity of water necessary for solubilizing it is added (solution 1); separately, a quantity of water necessary for solubilizing the carboxylic anionic polymer is added to the latter, the solubilization being promoted by neutralization with a traditional alkalinizing agent such as ammonia solution or alkanolamines (solution 2); the thickener is then formed by adding solution 1 with stirring to solution 2, or vice versa, at room temperature. A gel is thereby formed. This gel may be formed "in situ" during the preparation of the composition.

To prepare this thickener, the quaternized copolymer of cellulose or of the cellulose derivative is used in proportions of between 0.04 and 6% by weight, and preferably between 0.1 and 1.5% by weight, based on the total weight of the composition; the carboxylic anionic polymer is used in the proportion of 0.04 to 6% by weight, and preferably from 0.1 to 1.5% by weight, based on the total weight of the composition. The ratio by weight of the cationic polymer to the carboxylic anionic polymer is between 1:5 and 5:1, and preferably between 1:2 and 2:1, and more especially equal to approximately 1.

This thickening agent is used in the dentifrice compositions according to the invention, in proportions of between 0.2 and 12% by weight based on the total weight of the composition, and preferably in proportions of 0.5 to 3% by weight based on the total weight of the composition.

The abrasive agent is taken from the abrasives customarily used in dentifrice compositions, such as hydrated aluminas, anhydrous dicalcium phosphate, insoluble sodium metaphosphate, dicalcium phosphate dihydrate, or alkali metal or alkaline earth metal aluminosilicates, in proportions of between 5 and 75% by weight based on the total weight of the composition.

An especially preferred abrasive which gives especially advantageous results in the context of the invention is α-alumina trihydrate, used in proportions of between 10 and 60%, and preferably between 30 and 50% by weight based on the total weight of the composition.

The dentifrice compositions according to the invention can contain any other ingredients customarily used in these compositions, and more especially surfactants which are well known per se and are used for this type of application. These surfactants are chosen, in particular, from the nonionic surfactants of the poly(hydroxypropyl ether) family, such as the compounds corresponding to the following definitions:

(I)

in which $R_1$ denotes an alkyl radical or mixture of alkyl radicals containing from 10 to 14 carbon atoms, and m is an integer or decimal number from 2 to 10, and preferably from 3 to 6. These compounds may be prepared according to the process described in French Patent No. 1,477,048 or U.S. Pat. No. 3,578,719.

(ii) The compounds prepared by alkali-catalysed condensation of 2 to 10 moles, and preferably 2.5 to 6 moles, of glycidol with a $C_{10}$-$C_{14}$ alpha-diol or mixture of such alphadiols, at a temperature of 120°–180° C. and preferably 140° to 160° C., the glycidol being added slowly. Such products are prepared according to the processes described in French Patent No. A-2,091,516 or in U.S. Pat. No. A-3,821,372.

(iii) The compounds of formula:

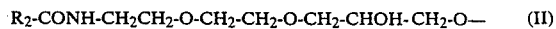

(II)

where $R_2$ denotes an alkyl and/or alkenyl radical or mixture of such radicals having from 11 to 17 carbon atoms, and p denotes an integer or decimal number from 1 to 5, and preferably from 1.5 to 4. These compounds may be prepared according to the process described in French Patent No. A-2,328,763 or U.S. Pat. No. 4,307,079.

(iv) The compounds prepared by acid-catalysed condensation of 2 to 10, and preferably 2.5 to 6 moles of glycidol per mole of alcohol or of alpha-diol containing 10 to 14 carbon atoms, at a temperature of 50° to 120° C., the glycidol being added slowly to the alcohol or alpha-diol. Such compounds may be prepared according to the process described in French Patent No. A-2,169,787.

The especially preferred surfactants are those derived from poly(hydroxypropyl ether) corresponding to the formulae:

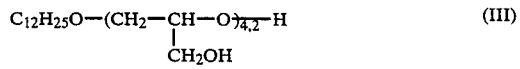

(III)

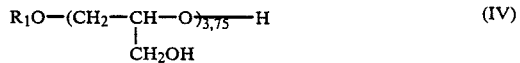

(IV)

where $R_1$ denotes a mixture of $C_{10}H_{21}$ and $C_{12}H_{25}$ alkyl radicals, and the compounds prepared by alkali-catalysed condensation of 3.5 moles of glycidol with a mixture of alphadiols having from 11 to 14 carbon atoms, according to the process described in French Patent No. A-2,091,516 or in U.S. Pat. No. 3,821,372, or of the compounds of formula:

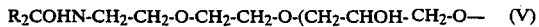
$$R_2COHN-CH_2-CH_2-O-CH_2-CH_2-O-(CH_2-CHOH-CH_2-O- \quad (V)$$

where $R_2$ denotes a mixture of alkyl or alkenyl radicals chosen from $C_{11}H_{23}$ and $C_{13}H_{27}$ radicals or the radicals derived from coconut fatty acids or from oleic acid.

Special preference is given to the compounds obtained by condensation of 3.5 moles of glycidol with a mixture of $C_{11}$-$C_{14}$ alpha-diols and prepared according to French Patent No. A-2,091,516 or U.S. Pat. No. b 3,821,372.

These surfactants are used in the gels according to the invention in concentrations which are generally between 0.1 and 4% by weight, preferably between 0.2 and 2% by weight, based on the total weight of the composition.

The compositions may also contain one or more bactericidal agents designed to combat the formation of dental plaque, and more especially cationic nitrogen compounds, among which the following may be mentioned by way of example:
diisobutylphenoxyethoxyethyldimethylbenzylammonium chloride; dodecyl trimethyl ammonium bromide; dodecyldimethyl-(2-phenoxyethyl)ammonium bromide; benzyldimethylstearylammonium chloride; cetylpyridinium chloride; quaternized 5-amino-1,3-bis(2-ethylhexyl)-5-methylhexahydroxypyrimidine; trimethylcetylammonium bromide; alkyldimethylhydroxyethylammonium bromide (where alkyl denotes a mixture of radicals derived from coconut fatty acids); chlorhexidine; alexidine; and cationic aliphatic tertiary amines.

These bactericidal agents are generally used in proportions of 0.005 to 10% by weight, and preferably 0.05 to 2% by weight, based on the total weight of the composition.

The dentifrice gels according to the invention can also contain a humectant in proportions of 10 to 80% based on the total weight of the composition. This humectant is chosen, for example, from glycerin, sorbitol, propylene glycol, and polyethylene glycols of low molecular weight such as polyethylene glycol 400 or polyethylene glycol 2000.

These compositions may contain sweetening agents at a concentration of between 0.1 to 2% by weight based on the total weight of the composition. By way of a sweetening agent, sucrose, lactose, fructose, xylitol, sodium cyclamate, maltose and sodium saccharinate may be mentioned.

They may contain a preservative, in a quantity between 0.01 to 0.5% by weight based on the total weight of the composition, such as, for example, formaldehyde and its derivatives, methyl parahydroxybenzoate, propyl parahydroxybenzoate and the like.

Flavouring agents which may be introduced into the compositions according to the invention are preferably used in proportions of 0.5 to 5% by weight based on the total weight of the composition. By way of flavouring substances, there may be mentioned essences of mint (spearmint or peppermint), of aniseed, or eucalyptus, of cinnamon, of clove, of sage and of liquorice, and essences of fruits such as lemon, orange, mandarin orange and strawberry, or, if desired, methyl salicylate.

The pH of these compositions is adjusted within usual ranges, and is more especially between 6 and 9 and preferably between 7 and 8.5. It is usually measured on a 20% dispersion of paste in water.

It is generally necessary to add acidifying agents, and citric acid, benzoic acid, monosodium phosphate and disodium phosphate may be mentioned by way of example.

The dentifrice gels contain, according to a preferred embodiment, an anti-caries agent which is known per se and more especially fluoride ion carriers. Among the latter, there may be mentioned, by way of example, soluble inorganic fluorides such as sodium, potassium, calcium, ammonium, zinc, tin, copper or barium fluoride; sodium or ammonium fluorosilicate, sodium or aluminium monofluorophosphate, aluminium difluorophosphate and sodium fluorozirconate. The most commonly used fluorine compounds are sodium fluoride, sodium monofluorophosphate and mixtures thereof.

The fluorine ion carrier is used at a concentration such that the fluorine ion content does not exceed 1500 ppm. By way of example, the concentrations used are, in the case of sodium fluoride, between 0.05 and 0.25%, and in the case of sodium monofluorophosphate, between 0.2 and 0.8% by weight.

The process for treating or cleaning the teeth consists in applying a composition as defined above by means of a brush, and in following this, after brushing, with a rinse.

The examples which follow are designed to illustrate the invention without, however, limiting it.

EXAMPLE 1

A dentifrice cream gel having the following composition is prepared:

| | |
|---|---|
| Methacrylic acid/ethyl monomaleate (72:28) copolymer, in aqueous solution containing 5% of AS and neutralized with 2-amino-2-methyl-1-propanol | 0.5 g AS |
| RHONE POULENC alumina SH 100 | 54.0 g |
| Copolymer of hydroxyethylcellulose grafted by means of a free-radical reaction with diallyldimethylammonium chloride, sold under the name "CELQUAT L 200" by the company NATIONAL STARCH, in 5% strength aqueous solution | 0.5 g AS |
| Non-ionic surfactant prepared by alkali-catalysed condensation of 3.5 moles of glycidol with a mixture of alpha-diols having from 11 to 14 carbon atoms, in aqueous solution containing 10% AS | 1.0 g AS |
| Flavouring, preservative qs | |
| Natural pH: | 7.9 |
| Water qs | 100.0 g |

EXAMPLE 2

A dentifrice cream gel having the following composition is prepared:

| | |
|---|---|
| Methacrylic acid/ethyl monomaleate (72:28) copolymer, in aqueous solution containing 5% of AS and neutralized with 2-amino-2-methyl-1-propanol | 0.5 g AS |
| Alumina SH 100 | 54.0 g |
| Copolymer of hydroxyethylcellulose grafted by means of a free-radical reaction with diallyldimethylammonium chloride, sold under the name "CELQUAT L 200" by the company NATIONAL STARCH, in 5% strength aqueous solution | 0.5 g AS |
| Non-ionic surfactant prepared by alkali- | |

| | |
|---|---|
| catalysed condensation of 3.5 moles of glycidol with a mixture of alpha-diols having from 11 to 14 carbon atoms, in aqueous solution containing 20% AS | 2.0 g AS |
| Flavouring, preservative qs | |
| Natural pH: | 7.7 |
| Sorbitol in 70% strength aqueous solution qs | 100.0 g |

EXAMPLE 3

A dentifrice cream gel having the following composition is prepared:

| | |
|---|---|
| Methacrylic acid/butyl methacrylate (65:35) copolymer, in aqueous solution containing 5% of AS and neutralized with 2-amino-2-methyl-1-propanol | 0.5 g AS |
| RHONE POULENC alumina SH 100 | 54.0 g |
| Copolymer of hydroxyethylcellulose grafted by means of a free-radical reaction with diallyldimethylammonium chloride, sold under the name "CELQUAT L 200" by the company NATIONAL STARCH, in 5% strength aqueous solution | 0.5 g AS |
| Non-ionic surfactant prepared by alkali-catalysed condensation of 3.5 moles of glycidol with a mixture of alpha-diols having from 11 to 14 carbon atoms, in aqueous solution containing 10% AS | 1.0 g AS |
| Flavouring, preservative qs | |
| pH: | 7.5 |
| Water qs | 100.0 g |

EXAMPLE 4

A dentifrice cream gel having the following composition is prepared:

| | |
|---|---|
| Methacrylic acid/diacetoneacrylamide (50:50) copolymer, in aqueous solution containing 5% of AS and neutralized with 2-amino-2-methyl-1-propanol | 0.5 g AS |
| RHONE POULENC alumina SH 100 | 54.0 g |
| Copolymer of hydroxyethylcellulose grafted by means of a free-radical reaction with diallyldimethylammonium chloride, sold under the name "CELQUAT L 200" by the company NATIONAL STARCH, in 5% strength aqueous solution | 0.5 g AS |
| Non-ionic surfactant prepared by alkali-catalysed condensation of 3.5 moles of glycidol with a mixture of alpha-diols having from 11 to 14 carbon atoms, in aqueous solution containing 10% AS | 1.0 g AS |
| Flavouring, preservative qs | |
| pH: | 7.6 |
| Water qs | 100.0 g |

EXAMPLE 5

A dentifrice cream gel having the following composition is prepared:

| | |
|---|---|
| Methacrylic acid/methyl methacrylate (50:50), copolymer in aqueous solution containing 5% of AS and neutralized with 2-amino-2-methyl-1-propanol | 0.4 g AS |
| RHONE POULENC alumina SH 100 | 54.0 g |
| Copolymer of hydroxyethylcellulose grafted by means of a free-radical reaction with diallyldimethylammonium chloride, sold under the name "CELQUAT L 200" by the company NATIONAL STARCH, in 5% strength aqueous solution | 0.4 g AS |
| Non-ionic surfactant prepared by alkali-catalysed condensation of 3.5 moles of glycidol with a mixture of alpha-diols having from 11 to 14 carbon atoms, in aqueous solution containing 10% AS | 1.0 g AS |
| Flavouring, preservative qs | |
| pH: | 7.6 |
| Water qs | 100.0 g |

EXAMPLE 6

A dentifrice cream gel having the following composition is prepared:

| | |
|---|---|
| Polymethacrylic acid, MW 137,000, in aqueous solution containing 5% of AS and neutralized with 2-amino-2-methyl-1-propanol | 0.3 g AS |
| RHONE POULENC alumina SH 100 | 54.0 g |
| Copolymer of hydroxyethylcellulose grafted by means of a free-radical reaction with diallyldimethylammonium chloride, sold under the name "CELQUAT L 200" by the company NATIONAL STARCH, in 5% strength aqueous solution | 0.3 g AS |
| Non-ionic surfactant prepared by alkali-catalysed condensation of 3.5 moles of glycidol with a mixture of alpha-diols having from 11 to 14 carbon atoms, in aqueous solution containing 10% AS | 1.0 g AS |
| Flavouring, preservative qs | |
| pH: | 7.5 |
| Water qs | 100.0 g |

EXAMPLE 7

A dentifrice cream gel having the following composition is prepared:

| | |
|---|---|
| Methacrylic acid/maleic acid (70:30) copolymer, in aqueous solution containing 5% AS and neutralized with 2-amino-2-methyl-1-propanol | 0.4 g AS |
| Copolymer of hydroxyethylcellulose grafted by means of a free-radical reaction with diallyldimethylammonium chloride, sold under the name CELQUAT H 100 by the company NATIONAL STARCH, in 5% strength aqueous solution | 0.6 g AS |
| Anhydrous dicalcium phosphate | 45.0 g |
| Nonionic surfactant of formula: $$C_{12}H_{25}O-(CH_2-CH-O)_{4.2}-H$$ $$\quad\quad\quad\quad\quad\quad\quad |\\ \quad\quad\quad\quad\quad\quad\quad CH_2OH$$ in aqueous solution containing 10% AS | 1.3 g AS |
| Flavouring, preservative qs | |
| Natural pH: | 6.85 |
| Water qs | 100.0 g |

EXAMPLE 8

A dentifrice cream gel having the following composition is prepared:

| | |
|---|---|
| Ethylene/maleic acid copolymer, in aqueous solution containing 1% AS and neutralized with 2-amino-2-methyl-1-propanol | 0.15 g AS |
| Copolymer of hydroxyethylcellulose grafted by means of a free-radical reaction with diallyldimethylammonium chloride, sold under the name CELQUAT H 100 by the company NATIONAL STARCH, in 5% strength aqueous solution | 0.3 g AS |
| Alumina SH 100 | 50.0 g |
| Nonionic surfactant of formula: R—CONH—(CH$_2$)$_2$—O—(CH$_2$)$_2$—O—(CH$_2$—CHOH—CH$_2$—O)$_{3,5}$H where R denotes the following mixture of alkyl and alkenyl radicals: 35% C$_{12}$H$_{25}$ - 15% C$_{14}$H$_{29}$ - 15% oleyl radicals - 35% radicals derived from coconut fatty acids, in 10% strength aqueous solution | 1.5 g AS |
| Flavouring, preservative qs | |
| Natural pH: | 7.75 |
| Water qs | 100.0 g |

EXAMPLE 9

A dentifrice cream gel having the following composition is prepared:

| | |
|---|---|
| Methacrylic acid/N—vinylpyrrolidone (80:20) copolymer, in aqueous solution containing 5% AS and neutralized with 2-amino-2-methyl-1-propanol | 0.5 g AS |
| Copolymer of hydroxyethylcellulose grafted by means of a free-radical reaction with diallyldimethylammonium chloride, sold under the name CELQUAT H 100 by the company NATIONAL STARCH, in 5% strength aqueous solution | 0.5 g AS |
| Anhydrous dicalcium phosphate | 45.0 g |
| Nonionic surfactant of formula: R—CONH—(CH$_2$)$_2$—O—(CH$_2$)$_2$—O—(CH$_2$—CHOH—CH$_2$—O)$_{3,5}$H where R denotes the following mixture of alkyl and alkenyl radicals: 35% C$_{12}$H$_{25}$ - 15% C$_{14}$H$_{29}$ - 15% oleyl radicals - 35% radicals derived from coconut fatty acids, in 10% strength aqueous solution | 0.8 g AS |
| Flavouring, preservative qs | |
| Natural pH: | 7 |
| Water qs | 100.0 g |

The dentifrices prepared according to Examples 1 to 9 possess a creamy gel texture, squeezing from the tube in the form of a ribbon whose consistency enables it to adhere on the brush without buckling. The pastes have a smooth and shiny appearance, are homogeneous and of constant viscosity. These creamy gels possess, moreover, good foaming power, not imparting a bitter taste and leaving the teeth smooth.

I claim:

1. Dentifrice composition, in the form of a creamy gel containing at least one abrasive agent in proportions of between 5 and 75% by weight based on the total weight of the composition, at least one thickening agent in proportions of between 0.2 and 12% by weight based on the total weight of the composition, wherein the said thickening agent results from the ionic interaction in aqueous medium between a cationic polymer, consisting of a copolymer of cellulose or cellulose derivative grafted with a water-soluble quaternary ammonium monomer salt, and a carboxylic anionic polymer having an absolute capillary viscosity in dimethylformamide or methanol, at a concentration of 5% and at 30 degrees C., of less than or equal to 0.08 Pa.s, this thickener having an Epprecht-Drage, module 3, viscosity in 1% strength solution in water at 25 degrees C. greater than or equal to 0.45 Pa.s, and a surfactant in proportions of between 0.1 and 4% by weight based on the total weight of the composition, said surfactant being selected from nonionic surfactants of the poly(hydroxypropyl ether) family.

2. Dentifrice composition according to claim 1, wherein the thickening agent results from the ionic interaction between a cationic polymer chosen from copolymers of hydroxyalkylcellulose grafted by means of a free-radical reaction with a water-soluble quaternary ammonium monomer salt chosen from methacryloylethyltrimethylammonium, methacrylamidopropyltrimethylammonium and dimethyldiallylammonium salts.

3. Dentifrice composition according to claim 1 wherein the thickening agent results from the ionic interaction of the said cationic polymer with a carboxylic anionic polymer chosen from homopolymers of methacrylic acid having a molecular weight, determined by light scattering, of more than 20,000; copolymers of methacrylic acid with one of the following monomers: a C$_1$–C$_4$ alkyl acrylate or methacrylate, an acrylamide derivative, maleic acid, a C$_1$–C$_4$ alkyl monomaleate and N-vinyl-pyrrolidone; and copolymers of ethylene and maleic anhydride.

4. Dentifrice composition according to claim 1 wherein the ratio by weight between the said cationic polymer and the carboxylic anionic polymer which are used for preparing the thickening agent is between 1:5 and 5:1.

5. Dentifrice composition according to claim 1 wherein the thickening agent results from the ionic interaction between 0.04 to 6% of cationic polymer as defined in claim 1 and 0.04 to 6% of carboxylic anionic polymer as defined in claim 1.

6. Dentifrice compositions according to claim 1 wherein the abrasive agent is chosen from hydrated alumina, anhydrous dicalcium phosphate, dicalcium phosphate dihydrate, insoluble sodium metaphosphate, and alkali metal or alkaline earth metal aluminosilicates.

7. Composition according to claim 1 wherein the abrasive agent is alumina present in proportions of between 10 and 60% by weight.

8. Composition according to claim 1, wherein the nonionic surfactant of the poly(hydroxypropyl ether) family is chosen from the following compounds:

(i) $R_1O-(CH_2-CHO)_m-H$ (I)
    $\qquad\quad\;\;|$
    $\qquad\quad\;\;CH_2OH$ in which $R_1$ denotes an alkyl group or mixture of alkyl groups containing 10 to 14 carbon atoms, and m is an integer or decimal number from 2 to 10, (ii) the compounds prepared by alkali-catalysed condensation of 2 to 10 moles of glycidol with a $C_{10}$-$C_{14}$ alpha-diol or mixture of such alpha-diols, (iii) $R_2\text{-CONH-CH}_2\text{-CH}_2\text{-O-CH}_2\text{-CH}_2\text{-O(CH}_2\text{-CHOH-CH}_2\text{-O)}_p\text{-----H (II) pos}$ in which $R_2$ denotes an alkyl and/or alkenyl radical or mixture of such radicals having 11 to 17 carbon atoms, and p denotes an integer or decimal number from 1 to 5, (iv) compounds prepared by acid-catalysed condensation of 2 to 10 moles of glycidol per mole of alcohol or of alpha-diol containing from 10 to 14 carbon atoms.

9. Composition according to claim 8, wherein the nonionic surfactant is chosen from the following compounds:

$C_{12}H_{25}O-(CH_2-CH-O)_{4.2}-H$
$\qquad\qquad\qquad\;\;|$
$\qquad\qquad\qquad\;\;CH_2OH$ $R_1O-(CH_2-CH-O)_{3.75}-H$
$\qquad\qquad\;\;|$
$\qquad\qquad\;\;CH_2OH$ in which $R_1$ denotes a mixture of $C_{10}H_{21}$ and $C_{12}H_{25}$ alkyl groups, and
the compounds prepared by alkali-catalyzed condensation of 3.5 moles of glycidol with a mixture of alpha-diols having 11 to 14 carbon atoms:

$R_2\text{-CONH-CH}_2\text{-CH}_2\text{-O-CH}_2\text{-CH}_2\text{-O-(CH}_2\text{-CHOH-CH}_2\text{-O)}-$ in which $R_2$ denotes a mixture of $C_{11}H_{23}$ and $C_{13}H_{27}$ alkyl radicals, or the alkyl and alkenyl radicals derived from coconut fatty acids and oleic acid.

10. Composition according to claim 1, containing, in addition, cationic nitrogenous bactericidal agents.

11. Composition according to claim 1 containing, in addition, sweetening agents, humectants, preservatives, flavouring agents and/or fluorine ion carriers.

12. Process for cleaning the teeth, comprising the application of at least one composition as defined in claim 1 on the teeth by means of a brush, and in that the teeth are rinsed after cleaning.

* * * * *